United States Patent [19]

Lalezari

[11] 4,418,059

[45] Nov. 29, 1983

[54] NUCLEOSIDE ESTER COMPOSITIONS

[75] Inventor: Iraj Lalezari, Scarsdale, N.Y.

[73] Assignees: Montefiore Medical Center; The Albert Einstein College of Medicine at Yeshiva University, both of New York, N.Y.; a part interest

[21] Appl. No.: 285,013

[22] Filed: Jul. 20, 1981

[51] Int. Cl.³ ...................... A61K 31/70; C07H 17/00
[52] U.S. Cl. ..................................... 424/180; 536/23; 260/397.1
[58] Field of Search ........................... 424/180; 536/23

[56] References Cited

U.S. PATENT DOCUMENTS 3,282,921 11/1966 Verheyden et al. ................. 536/23
3,856,777 12/1974 Ishido et al. .......................... 536/23
4,211,773 7/1980 Lopez et al. ........................ 536/23

OTHER PUBLICATIONS

Nishizawa et al., "Biochemical Pharmacology", vol. 14, (1965), pp. 1606–1619.

*Primary Examiner*—Elbert L. Roberts
*Attorney, Agent, or Firm*—Hedman, Casella, Gibson, Costigan & Hoare

[57]     ABSTRACT

A composition comprising a nucleosidic anti-tumor agent esterified with a carboxylic acid-containing steroid is described. These steroid ester derivatives of, for example, a deoxyuridine compound provide enhanced anti-tumor effects in chemotherapy as compared to the corresponding nucleosides alone.

5 Claims, No Drawings

NUCLEOSIDE ESTER COMPOSITIONS

BACKGROUND OF THE INVENTION

Many nucleosides have a proven efficacy in the chemotherapeutic treatment of various tumor systems. These nucleosides, and particularly deoxyuridine compounds and purine or pyrimidine nucleosides, have been successfully utilized for treatment of human neoplasms of the breast, colon, liver and gastro-intestinal system.

Notwithstanding the results achieved to date with these nucleosides, enhancement and focus of their effects remains desirable. These are the primary objectives of the present invention.

SUMMARY OF THE INVENTION

The present invention is directed to derivatives of nucleosidic anti-tumor agents. These derivatives of nucleosides have an increased efficacy for chemotherapeutic treatment. It has been discovered that certain esters of, in particular the dioxyuridine compounds, possess this heightened activity.

The esters are formed from carboxylic acid-containing steroids. These esters of, for example, bile acids may be administered alone or in combination with a conventional carrier-diluent to produce relatively increased anti-tumor activity.

DETAILED DESCRIPTION OF THE INVENTION

The nucleosides utilized in accordance with the present invention are well-known. They comprise those glucoside-like complexes of a nitrogen-containing base and a carbohydrate which possess anti-tumor activity. Preferred examples of these nucleosides are the deoxyuridines, including halo-deoxyuridines such as 5-bromo-2-deoxyuridine and especially 5-fluoro-2-deoxyuridine. Also included are the purine and pyrimidine nucleosides of, for example, ribose or deoxyribose. In particular, azo and mercapto derivatives of the bases of these nucleosides are desirable. Such compounds, per se are already accepted for use in chemotherapeutic treatment of tumors.

The remainder of the present esters is derived from a carboxylic acid-containing steroid. Any steroid moiety, synthetic or naturally occurring, may be employed. Similarly, the steroid may natively possess a carboxylic group—as in the case, for example, of bile acids—or such a carboxylic group may be incorporated in conventional manner into a non-acidic steroid moiety. Typical non-acidic steroid moieties susceptible to use in this latter manner include sex hormones—such as progesterone—and the like.

In accordance with the present invention, the nucleosides are esterified through one or more of their alcohol groups. In preferred embodiments, an oligo-ester having from 2 to 4 separate ester groups is formed. Although different carboxylic acid-containing steroids may be used to form these groups, they are desirably the same.

Actual production of the present esters may in many cases be performed in conventional manner through an intermediate acyl chloride derivative of the carboxylic acid-containing steroid to facilitate reaction with the nucleoside. In some instances, however, this technique leads to extremely low yields. This is particularly true where the steroid itself contains one or more active sites, including oxygens such as alcohol and ketone groups or amine groups, which could interfere with the production of the intermediate through use of conventional acylchloride reaction techniques.

Accordingly, a preferred means of forming the esters of the present invention involves the use of mixed steroid anhydride for reaction with the nucleoside. This process is described in detail in a companion patent application Ser. No. 285,282 of this inventor filed concurrently herewith and incorporated herein by reference.

In accordance with this preferred means, the desired carboxylic acid-containing steroid may first be reacted with the lower alkyl ester of a chloro-carbonic acid. The reaction should take place in an inert organic solvent in the presence of a Lewis base to allow quantitative conversion to the mixed anhydride. The mixed anhydride may then be reacted with the nucleoside under reflux conditions to yield an ester of the present invention.

Although not wishing to be bound by such theory, it is believed that at least a portion of the enhanced efficacy of the present esters derives from the ability to focus their activity through selection of particular steroid moieties. As is known, given steroids tend to concentrate in different organs of the body. Consequently, the present invention allows a means for conveying a nucleoside's activity to tumors located in such organs through the simple expedient of selection of an appropriately organ-specific steroid for esterification.

In the case of a liver tumor, for example, an ester derived from a bile acid is desirably utilized for chemotherapeutic treatment. Because bile acids are actively taken up by hepatic tissue, they tend to target that area. This at least partially explains the enhanced efficacy of such esters of bile acids on primary hepatomas and metastatic hepatic neoplasms.

For utilization, the esters of the present invention are normally first admixed with an inert carrier-diluent. For oral ingestion, a solid carrier such as starch or sugar may be employed to produce a pill. For injection, a liquid solvent such as propylene glycol is preferred.

In dosage form, the ester is normally utilized in an amount in excess of 20, preferably from about 100 to 400, milligram/day/50 kilogram of body weight. Consequently, the amount of carrier-diluent employed is desirably greater than the weight of ester.

The present invention may be more fully understood by reference to the following example which should be construed as illustrative and in no way to limit the scope of the present invention.

EXAMPLE

Preparation of Mixed Anhydride 1.14 ml (0.12 mole) of ethyl chloro-carbonate is added dropwise to a room temperature solution of 4.71 g (0.12 mole) of deoxycholic acid and 3 ml of triethylamine in 75 ml of tetrahydrofuran. A precipitate of triethylammonium chloride salt forms almost immediately. After 10 minutes of stirring, the salt is separated by filtration and the remaining solution is then evaporated under reduced pressure to yield a transparent mass which is the mixed anhydride.

Preparation of 5-Fluoro-2-Deoxyuridine-Di-Deoxycholate 0.98 g (4 m mole) of 5-fluoro-2-deoxyuridine is added to the mixed anhyride in tetrahydrofuran as prepared above. The mixture is refluxed for 8 hours. 100 ml of water is added and the organic solvent is evaporated under reduced pressure. The product is then extracted with chloroform, washed with concentrated aqueous sodium bicarbonate and finally with water.

The thus purified product is subjected to preparative thin layer chromatography using fluorescent silica gel plates. The plates are eluted with a 6:1 mixture of chloroform and methanol. The desired diester is separated with acetone and then repeatedly precipitated with hexane from ethyl acetate solutions to effect final purification.

The final product (3.14 g or a yield of 79%) is a white powder having a melting point of 162°–165° C. A comparison of the actual of elemental analysis, confirming a diester of the composition $C_{24}H_{50}N_2O_3$, is as follows:

|  | C | H | N |
| --- | --- | --- | --- |
| (calculated) | 68.81 | 8.75 | 2.91 |
| (found) | 69.08 | 8.81 | 2.73 |

ACTIVITY TEST A

The activity of the diester is examined in cell cultures of human hepatomas and leukemia. In addition to diester, comparative cultures are also grown in the presence of 5-fluoro-2-deoxyuridine, both alone and in combination with diester. The diester shows a significantly greater suppression of tumorous cell activity than any of the other runs.

ACTIVITY TEST B

The relative toxicities of the diester and of 5-fluoro-2-deoxyuridine are examined for mice. The diester is found to be approximately 19 times as potent.

Mice having induced tumors are then given LD-10 injections of the diester in oil over a thirty-four (34) day period as follows:

| Day 0 | 2.8 mg diester |
| --- | --- |
| Day 19 | 2.0 mg diester |
| Day 25 | 2.0 mg diester |

A control groups of mice are given similar LD-10 interperitoneal injections of deoxyuridine in olive oil.

During the test period, the mice are examined periodically for tumor size to determine differences in their rates of growth (or, correspondingly, anti-tumor activity). The results are as follows:

|  | Tumor Size (mm.) | |
| --- | --- | --- |
| Day | Control | Diester |
| 0 | 2.6 | 3.0 |
| 6 | 5.0 | 4.4 |
| 11 | 10.0 | 6.4 |
| 15 | 12.2 | 8.6 |
| 20 | 14.9 | 11.8 |
| 25 | 18.6 | 13.6 |
| 29 | 20.7 | 16.0 |
| 34 | 23.5 | 17.4 |

This data indicates that the rate and degree of growth of tumors in mice injected with the diester is consistently less. The high significance of this data ($P<0.001$) proves the anti-tumor activity of the present compositions. Thus the diester offers substantial improvement over the known anti-tumor agent from which it is derived.

The above mentioned patent application is incorporated herein by reference. Obviously, modifications and variations of the present invention are possible in light of its and other known teachings. It is therefore to be understood that changes may be made in the particular embodiments of the invention described which are within the full intended scope of the invention as defined by the appended claims.

What is claimed is:
1. An ester of a halo deoxyuridine selected from the group consisting of 5-bromo-2-deoxyuridine and 5-fluorodeoxyuridine and a bile acid.
2. The ester of claim 1, wherein said ester is admixed with an inert carrier.
3. The composition of claim 2, wherein the carrier is present in an amount by weight greater than the amount of ester.
4. An ester of a nucleosidic anti-tumor agent and a carboxylic acid-containing bile acid, wherein the ester is of 5-fluoro-2-deoxyuridine and deoxycholic acid.
5. The ester of claim 4 wherein said ester is admixed with an inert carrier.

* * * * *

UNITED STATES PATENT OFFICE
CERTIFICATE OF CORRECTION

Patent No. 4,418,059          Dated November 29, 1983

Inventor(s) Iraj Lalezari

It is certified that error appears in the above-identified patent and that said Letters Patent are hereby corrected as shown below:

On the title page item [75] the following should be added:

--Steven Fox, Paoli, Pennsylvanis as co-inventor--.

Signed and Sealed this

Third Day of April 1984

[SEAL]

Attest:

Attesting Officer

GERALD J. MOSSINGHOFF

Commissioner of Patents and Trademarks